United States Patent
Frey et al.

(10) Patent No.: US 10,639,070 B2
(45) Date of Patent: May 5, 2020

(54) IMPLANT NEEDLE AND METHOD FOR PRODUCTION

(71) Applicant: Roche Diabetes Care, Inc., Indianapolis, IN (US)

(72) Inventors: Stephan-Michael Frey, Griesheim (DE); Oliver Kube, Worms (DE); Andrea Rittinghaus, Neckarsteinbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 117 days.

(21) Appl. No.: 15/246,188

(22) Filed: Aug. 24, 2016

(65) Prior Publication Data

US 2016/0361091 A1 Dec. 15, 2016

Related U.S. Application Data

(63) Continuation of application No. PCT/EP2015/053647, filed on Feb. 20, 2015.

(30) Foreign Application Priority Data

Feb. 26, 2014 (EP) .................... 14156876

(51) Int. Cl.
*A61B 17/34* (2006.01)
*A61M 5/32* (2006.01)
*A61B 17/00* (2006.01)

(52) U.S. Cl.
CPC ...... *A61B 17/3468* (2013.01); *A61B 17/3421* (2013.01); *A61B 2017/00526* (2013.01); *A61B 2017/3454* (2013.01); *A61M 5/3286* (2013.01)

(58) Field of Classification Search
CPC .......... A61B 17/06066; A61B 17/3421; A61B 17/3468; A61B 2017/00526;
(Continued)

(56) References Cited

U.S. PATENT DOCUMENTS 2,904,045 A * 9/1959 Owings ............... A61M 5/3286
604/274
3,064,651 A * 11/1962 Henderson .......... A61M 5/3286
604/274

(Continued)

FOREIGN PATENT DOCUMENTS

CN 101056664 A 10/2007
DE 102 24 101 A1 12/2003
(Continued)

OTHER PUBLICATIONS

Moore et al., Modeling of the Plane Needle Cutting Edge Rake and Inclination Angles for Biopsy, Oct. 2010, Journal of Manufacturing Science and Engineering, vol. 132, pp. 051005-1 to 051005-8. (Year: 2010).*

(Continued)

*Primary Examiner* — Robert A Lynch
(74) *Attorney, Agent, or Firm* — Bose McKinney & Evans LLP

(57) ABSTRACT

Disclosed is an implant needle for introducing an implant into a patient. The needle has a hollow main body having a receiving portion configured to receive an implant. A taper-shaped tip portion is cut from the hollow needle main body and includes a first slant surface contiguous to an outer peripheral surface of the main body and formed at a first predetermined angle with respect to an axis of the main body. The first slant surface has an inner non-cutting edge and an outer non-cutting edge. The needle also includes a pair of second slant surfaces, each of which forms a second predetermined angle with respect to the main body axis that is larger than the first predetermined angle. Each second slant surface has an inner non-cutting edge and an outer cutting edge that is contiguous with an edge point of the tip (Continued)

portion. A method of manufacturing the implant needle is also disclosed.

15 Claims, 1 Drawing Sheet

(58) Field of Classification Search
CPC . A61B 2017/06071; A61B 2017/3454; A61M 5/158; A61M 5/1585; A61M 5/3286; A61M 25/001
See application file for complete search history.

(56) References Cited

U.S. PATENT DOCUMENTS

| | | | | |
|---|---|---|---|---|
| 3,071,135 | A * | 1/1963 | Baldwin | A61M 5/3286 604/274 |
| 3,448,740 | A | 6/1969 | Figge | |
| 3,768,211 | A * | 10/1973 | Da Costa | B21G 1/006 451/102 |
| 4,490,139 | A | 12/1984 | Huizenga et al. | |
| 5,484,422 | A * | 1/1996 | Sloane, Jr. | A61M 25/0009 604/272 |
| 5,536,259 | A * | 7/1996 | Utterberg | A61M 5/3286 604/272 |
| 5,575,780 | A * | 11/1996 | Saito | A61M 5/3286 604/264 |
| 5,752,942 | A * | 5/1998 | Doyle | B24B 19/16 604/274 |
| 5,853,391 | A * | 12/1998 | Bell | A61B 17/3401 604/160 |
| 6,936,006 | B2 * | 8/2005 | Sabra | A61B 5/14532 600/300 |
| 2002/0188247 | A1 | 12/2002 | Peery | |
| 2003/0225361 | A1 * | 12/2003 | Sabra | A61B 5/14532 604/19 |
| 2006/0235446 | A1 * | 10/2006 | Godin | A61B 17/0401 606/151 |
| 2010/0324579 | A1 | 12/2010 | Bardy | |
| 2012/0116322 | A1 * | 5/2012 | Brink | A61B 10/0233 604/264 |
| 2014/0236104 | A1 | 8/2014 | Haindl | |
| 2014/0243844 | A1 * | 8/2014 | Clancy | A61M 37/0069 606/117 |
| 2017/0049514 | A1 * | 2/2017 | Cosman | A61N 1/0551 |

FOREIGN PATENT DOCUMENTS

| | | |
|---|---|---|
| DE | 10 2011 112 021 A1 | 2/2013 |
| FR | 1 225 009 | 6/1960 |
| NL | 8902938 A | 6/1991 |
| WO | WO 99/53991 A1 | 10/1999 |
| WO | WO 2005/044116 A2 | 5/2005 |

OTHER PUBLICATIONS

English Translation State Intellectual Property Office, P.R. China, First Office Action, CN201580010563.1, dated Nov. 27, 2017, 8 pages.

* cited by examiner

IMPLANT NEEDLE AND METHOD FOR PRODUCTION

RELATED APPLICATIONS

This application is a continuation of PCT/EP2015/053647, filed Feb. 20, 2015, which claims priority to EP 14 156 876.6, filed Feb. 26, 2014, both of which are hereby incorporated herein by reference in their entireties.

BACKGROUND

The invention relates to an implant needle for introducing an implant into a body of a patient and a method for production.

For inserting implants, e.g., sensors, into the skin up to an insertion depth of approximately 10 mm different types of implant cannula or needles are known, e.g., closed cannulas with a V-bevel, oval-shaped slotted cannulas with a V-bevel, and peel catheters, i.e., a cannula tube divided into two with a V-bevel which is then opened in the skin and removed in separate parts.

A flat sensor cannot be inserted into the skin with closed implant needles with a V-bevel, tubular. Oval-shaped slotted implant cannulas or needles are more expensive to manufacture than tubular slotted cannulas. They are predominantly used for 90° insertion angles. Peel catheters are also more expensive to manufacture and usually are only allowed to be inserted and removed by a doctor or nurse.

Document DE 10 2011 112 021 A1 discloses a needle or cannula provided with a tapered tip portion. Also, Document DE 102 24 101 A1 refers to cannula provided with a tapered tip portion. There are a first slant surface provided contiguous to an outer peripheral surface of the hollow needle main body and a pair of second slant surfaces contiguous to the first slant surface and symmetric with respect to an edge point and the axis of the hollow needle main body.

Document WO 99/53991 A1 refers to an implant retention trocar which includes a cannula for puncturing the skin of an animal and an obturator for delivering the implant beneath the skin of the animal. The implant retention trocar has a cannula distal tip design which causes a minimum of trauma and tearing of tissue during implant insertion. A spring element received within the cannula prevents an implant which is to be inserted into an animal from falling out of the cannula during the implant insertion process. The spring element includes a longitudinal leg which is folded with a zig-zag shaped bend. When the spring element is inserted into the cannula the zig-zag shaped bend of the shaped bend of the longitudinal leg retains the implant within the cannula.

Document US 2010/324579 discloses an instrument with a covered bore for subcutaneous implantation. An incising body defines a non-circular coaxial bore and includes a sharpened cutting edge that extends from a bottom distal end beyond the opening of the coaxial bore and an attachment point at a top distal end. A plunger is non-fixedly contained within the coaxial bore and slides longitudinally therein. A cover is pivotally attached at the attachment point and extends down to the bottom distal end and, when closed, the cover encloses the opening proximal to the cutting edge.

Document U.S. Pat. No. 3,064,651 relates to a hypodermic needle comprising an axial bore and being beveled at its outer end to provide a tissue penetrating tip and an obliquely disposed bore orifice extending rearwardly from said tip.

Document U.S. Pat. No. 3,448,740 refers to a noncoring hypodermic needle, comprising a heel portion and a tip portion terminating in a piercing point characterized in that at least one side wall portion is spirally curved from the piercing point to the heel portion and the heel portion is rotatably displaced approximately within the range of 260° to 280° and preferably about 270° from the piercing point in the same direction as the direction of spiral of said side wall portion.

Document WO 2005/044116 discloses a cutting device for a blunt needle or transcutaneous sensor for insertion through the derma of a patent, said blunt needle or transcutaneous sensor having a circumference at the distal end, said cutting device comprising a base part and a cutting member for making an incision in the derma, said base part having a track adapted for slideable engagement with the needle or transcutaneous sensor, wherein the cutting member has a cutting width, W, being less than half the length of the circumference of the blunt needle or transcutaneous sensor.

Document U.S. Pat. No. 4,490,139 refers to a subcutaneous implant needle formed as a hollow tube having its forward end cut on a plane at an acute angle to the central axis of the tube to form an elliptical opening, and an elliptical outer edge having a sharp forward portion. The forward extremity of the needle is dressed to form cutting edges intersecting at an obtuse angle and forming a central point. The dressed edges have a width preferably less than two-thirds the diameter of the tube, and the adjoining side portions of the elliptical outer edge are rendered unsharp and dulled, as by abrasion such as sandblasting or tumbling in abrasive media. The needle is dimpled at two locations closely adjacent the rear of the opening.

SUMMARY

Disclosed is an improved implant needle for introducing an implant, for example a sensor device, into a body of a patient, and a method for production. On the one hand, the implant needle allows for un-destructive implantation of the implant. Further, on the other hand, the implant needle shall support conservative implantation into the patient's body.

According to one aspect, an implant needle for introducing an implant into a body of a patient is provided. The implant needle comprises a receiving portion configured to receive an implant and provided in a hollow needle main body, and a taper-shaped tip portion formed by cutting a tip portion of the hollow needle main body. The implant needle may also be referred to an implant cannula.

The taper-shaped tip portion comprises a first slant surface provided contiguous to an outer peripheral surface of the hollow needle main body. The first slant surface is formed at a predetermined angle with respect to an axis of the needle main body. The first slant surface may also be referred to as primary or base cut.

The taper-shaped tip portion further comprises a pair of second slant surfaces contiguous to the first slant surface and symmetric with respect to an edge point and the axis of the hollow needle main body. The pair of second slant surfaces is formed at a larger angle with respect to the axis of the needle main body than the predetermined angle with respect to the axis of the needle main body. The pair of second slant surfaces may also be referred to as facet cut.

An outer edge of the pair of second slant surfaces is provided as a cutting edge contiguous to the edge point. The inner and outer edges of the first slant surface are provided as non-cutting edges.

The first slant surface and the pair of second slant surfaces are provided in a bevel of the implant needle. The angle at which the first slant surface is formed with respect to the axis of the needle main body, for example, may be from 14° to 16°, preferably about 15°. The angle at which the pair of second slant surfaces is formed with respect to the axis of the needle main body, for example, may be from 22° to 26°, preferably from 23° to 25°.

According to another aspect a method for production of the implant needle is provided. The method comprises: Providing a hollow needle main body having a lumen surrounded by a peripheral wall; producing a receiving portion configured to receive an implant and provided in the hollow needle main body; and producing a taper-shaped tip portion formed by cutting a tip portion of the hollow needle main body, wherein the taper-shaped tip portion is produced with a first slant surface contiguous to an outer peripheral surface of the hollow needle main body and formed at a predetermined angle with respect to an axis of the needle main body, and a pair of second slant surfaces contiguous to the first slant surface and symmetric with respect to an edge point and the axis of the needle main body and formed at a larger angle with respect to the axis of the needle main body than the predetermined angle with respect to the axis of the needle main body. Further, an outer edge of the pair of second slant surfaces is produced as a cutting edge contiguous to the edge point, and inner and outer edges of the first slant surface are produced as non-cutting edges. Preferably, with respect to the inner and outer edges of the first slant surface, the non-cutting edges are produced by applying abrasive material blasting only. As an alternative, material blasting may be used for finishing the non-cutting edges after basic edge rounding was produced by a different technique such as grinding and/or electropolishing.

The implant needle may be made of at least one material selected from the following group of materials: glass, ceramic, plastic material and metal.

An implant device may be provided by placing an implant in the receiving section of the implant needle. For example, a sensor device may be placed in the receiving section. The implant may have a flat shape fitting removable into the receiving section of the hollow needle main body.

The implant needle proposed is designed for a preferred use at an insertion angle of 45° to 90°.

The first slant surface may be provided as a pair of first slant surfaces symmetric with respect the axis of the needle main body. In such embodiment, the bevel may be provided as a V-bevel.

An inner edge of the pair of second slant surfaces as whole or in part may be provided as non-cutting edges.

The receiving portion may be formed contiguous to the taper-shaped tip portion.

In an embodiment, the receiving portion comprises a recess or opening extending through the needle main body. The recess may be contiguous to the bevel provided in the taper-shaped tip portion. In such embodiment, the recess is opened to the bevel.

At least an inner edge of one or more surfaces surrounding the recess may be provided as non-cutting edge.

The recess may be formed symmetric with respect to the axis of the needle main body. The recess may comprise or may be formed as a slit recession which may be formed contiguous to the pair of second slant surfaces.

The pair of second slant surfaces may be formed contiguous to the first slant surface.

In some embodiment, the hollow needle main body may be provided with one of a round cross-section and an oval cross-section.

One or more of the non-cutting edges may be provided as rounded edges. In the process of production, such rounding may be provided by grinding and/or electropolishing. In addition or as an alternative, abrasive material blasting may be used. For example, with respect to edges the first slant surface abrasive material blasting was found to be preferred for providing sufficient rounding in the process of production.

The hollow needle main body may be provided with a U- or V-shaped cross section in at least one of the receiving portion and the taper-shaped tip portion. With respect to the taper-shaped tip portion, a U- or V-bevel may be provided.

The hollow needle main body may be provided with a diameter of 0.6 mm to 1.2 mm.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
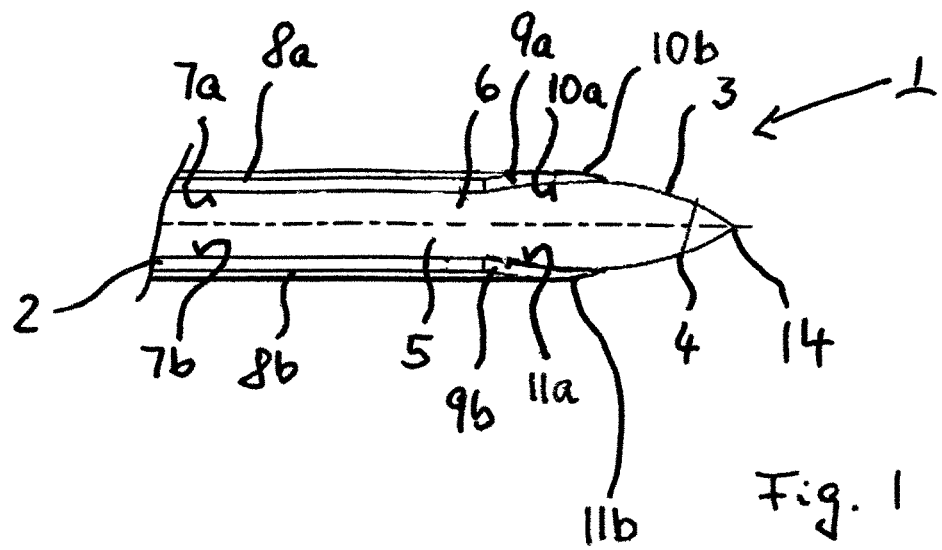
FIG. 1 a top view of a tip section of an implant needle having a hollow needle or cannula main body provided with taper-shaped tip portion.
Figure 2:
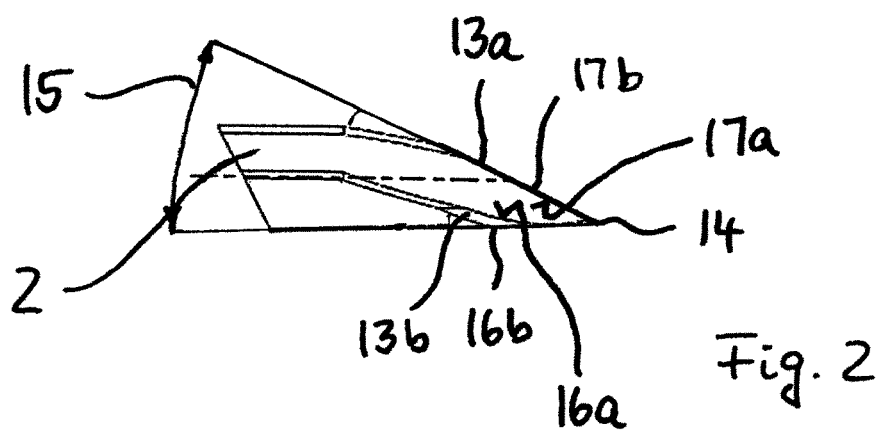
FIG. 2 perspective view of a tip part of the tip section in FIG. 1.
Figure 3:
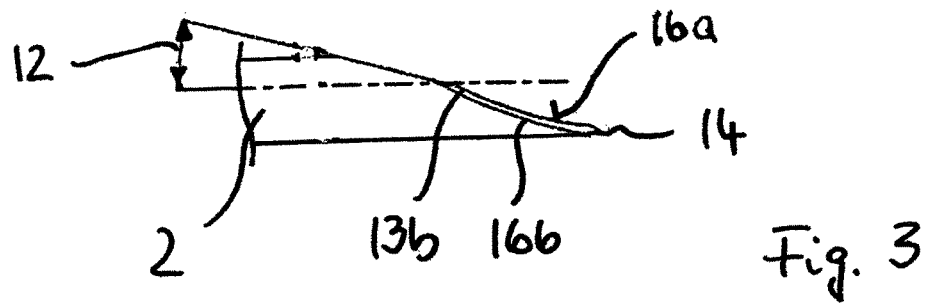
FIG. 3 a side view of the tip part of the in FIG. 2.

Referring to FIGS. 1 to 3, an implant needle 1 having a hollow needle or cannula main body 2 is provided. The hollow needle main body 2 is provided with taper-shaped tip portion 3 at an end 4.

The hollow needle main body 2 comprises a receiving section 5 provided with a slot opening 6 in the embodiment shown. The receiving section 5 is configured to receive an implant element (not shown), e.g., a sensor, to be introduced into the body of a human being or an animal through the skin by the implant needle 1. For implantation the implant is located in the receiving section 5. After puncturing through the skin into the body, the implant needle 1 is retracted leaving the implant in the body. When the implant needle 1 is retracted the implant element slides out of the receiving section 5.

Inner edges 7a, 7b formed in the range of the slot opening 6 or the receiving section 5 are provided as non-cutting edges. This will also support preventing the implant element from damage when the implant element is leaving the receiving section 5 during implantation. Also, outer edges 8a, 8b are provided as non-cutting edges.

In the taper-shaped tip portion 3 formed by cutting the hollow needle main body 2 at the end 4, a pair of first slant surfaces 9a, 9b is provided. The pair of first slant surfaces 9a, 9b is formed contiguous to the slot opening 6. Inner as well as outer edges 10a, 11a, 10b, 11b of the first slant surfaces 9a, 9b are provided as non-cutting edges. The non-cutting edges may be produced by rounding edges after cutting the material. The pair of first slant surfaces 9a, 9b is formed symmetric with respect to the axis of the needle main body 2 and at an angle 12 with respect to the axis of the needle main body 2 (see FIG. 3). The angle 12 at which the pair of first slant surfaces 9a, 9b is formed with respect to the axis of the needle main body 2, for example, may be from 14° to 16°, preferably about 15°.

In the taper-shaped tip portion 3, contiguous to the pair of first slant surfaces 9a, 9b a pair of second slant surfaces 13a, 13b is formed. The pair of second slant surfaces 13a, 13b is formed symmetric with respect to an edge point 14 and the axis of the needle main body. The edge point 14 leads to low initial force on penetration of the skin. The cut may be achieved through faceting and a slight point retraction.

For the pair of second slant surfaces 13a, 13b an angle 15 (see FIG. 2) with respect to the axis of the needle main body 2 is larger than the angle 12 provided for the pair of first slant surfaces 9a, 9b. The angle 15 at which the pair of second slant surfaces 13a, 13b is formed with respect to the axis of the needle main body 2, for example, may be from 22° to 26°, preferably from 23° to 25°. The pair of second slant surfaces 13a, 13b extends approximately along half the diameter of the needle main body 2.

Outer edges 16b, 17b of the pair of second slant surfaces 13a, 13b are provided as cutting edges. Inner edges 16a, 17a of the pair of second slant surfaces 13a, 13b are provided as non-cutting edges. In conclusion, the outer edges 16b, 17b will cut the skin, the inner edges 16a,17a will not do this which is to avoid punch effects. Together, the edge point 14 and cutting outer edges 16b, 17b result in a straight or slightly U-shaped wound incision pattern. The length of the wound incision is thus considerably shorter than the outer diameter of the implant needle 1 and thus much shorter than its circumference, i.e., the skin is stretched on insertion of the implant needle or cannula 1.

The pair of first slant surfaces 9a, 9b and the pair of second slant surfaces 13a, 13b provide for a V-bevel in the taper-shaped tip portion 3.

The implant needle 1 may be used for introducing a sensor element, e.g., a sensor having a flat shape, in the field of continuous glucose measurement (CGM). The slot opening 6 is to enable a contacting end of the sensor (not shown) to be placed in a position outside the interior space (lumen) of the needle main body 2. In the retraction during the insertion process the slot opening 6 is necessary in order to be able to retract the implant needle 1 when the senor has been inserted without changing the position of the sensor. For this the inner edges 7a, 7b are rounded so as not to damage the neck of sensor when pulling the implant needle 1 out (retraction). This is also important when inserting the sensor into the implant needle 1. Such non-cutting slot edge(s) is also important in order not to cause unnecessary injury to the skin when inserting and retracting the implant needle 1.

Non-cutting edges, for example, can be produced by grinding or laser cutting or water cutting. In addition, finishing through blasting with materials or polishing may be used for rounding the edge. Blasting can be carried out with, for example, glass spheres, corundum, and sand. A well-known method is polishing, in this case typically electropolishing in fluid, i.e., with the aid of an applied electrical field, material peaks with a high field line concentration are removed. The required "major" rounding is not produced by electropolishing.

In the case of finishing by way of material blasting, the blasting angle, blasting material, blasting density, the pressure etc. on the edge to be rounded, and the position of the blasting nozzle are decisive. For inserting sensors in slotted implant needles with a rounded edge, blasting of the slot edge from the direction of the V-bevel, i.e., in parallel to the axis of the needle main body 2 has proven to be beneficial. It can also take place at a shallow angle from the V-bevel, or at a shallow angle from the tube side. If carried out perpendicularly to the slot edge or at larger angles thereto blasting may likely cause damage.

With respect to the inner and outer edges 10a, 11a, 10b, 11b of the first slant surfaces 9a, 9b, in order to round off the edges sufficiently, material blasting may preferably be used. Different to the situation with respect to the inner and outer edges 7a, 7b, 8a, 8b, it was found that neither grinding nor electropolishing could provide sufficient edge rounding. For the material blasting the section with the pair of second slant surfaces 13a, 13b is suitably covered in order to prevent the cutting edges being damaged. Again, blasting in parallel or at a shallow angle to the needle main body axis is advantageous in order to avoid damage to the blasted edges.

A slotted implant needle with a V-bevel has the advantage that not the entire cross-sectional area of a complete tube has to be displaced during sensor element insertion. The insertion forces are therefore lower. The patient appreciates this through a reduced sensation of pain. Technically seen the insertion mechanism has to apply less force and can thereby be dimensioned in a smaller and more cost-effective manner.

In use the implant needle design results in short wound incisions, thus little pain and a reduction in the tendency to bleed, both of which are important to the patient. As cutting only takes place for a short distance and the circumferential line of the implant needle is a multiple of the wound incision length, the cells, nerve cells and blood vessels in the skin are largely displaced unharmed by the cannula and not predominantly cut. These positive results may only be achieved through finishing treatment of the V-bevel, not by having the bevel as such.

A well-designed V-bevel, combined with the finishing proposed, results in lower penetration forces in the skin, as achieved with siliconized needles. Siliconization can therefore also be dispensed with. This may be more cost-effective and for the customer there is no risk of worn-off silicone accumulating in the body.

The described design of the edges also has advantages in mounting the sensor in the slot opening 6. It is pulled into the implant needle 1 from the point of the needle in parallel to the axis of the needle. Through the described rounding of the edge and the shape of the slot, damage during the mounting process is prevented. The design of the V-bevel ensures a very position error-tolerant insertion of the sensor. It can also take place more quickly which saves production costs and time.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. An implant needle for introducing an implant into a body of a patient, comprising:
   a hollow needle main body having a main body axis, an outer peripheral surface and a receiving portion, the receiving portion configured to receive an implant; and
   a taper-shaped tip portion cut from the hollow needle main body, the taper-shaped tip portion having an edge point, wherein, when viewed from a position diametrically opposite the edge point, the taper-shaped tip portion tapers inwardly toward the edge point, and further comprising:

a first slant surface contiguous to the outer peripheral surface and formed at a first predetermined angle with respect to the main body axis, the first slant surface having an inner non-cutting edge and an outer non-cutting edge; and a pair of second slant surfaces each symmetric with respect to the edge point and the main body axis, each second slant surface forming a second predetermined angle with respect to the main body axis that is larger than the first predetermined angle, and each second slant surface having a non-cutting rounded inner edge and a cutting outer edge wherein the two cutting outer edges meet at and are contiguous to the edge point and thereby define a non-rounded pointed tip at the edge point;

wherein the needle main body defines a first transverse axis extending perpendicular to the main body axis and intersecting both the main body axis and the edge point, and a second transverse axis extending perpendicular to both the main body axis and the first transverse axis and intersecting the main body axis, the first slant surface being visible from a position external to the outer peripheral surface on the first transverse axis diametrically opposite the edge point, a respective one of the pair of second slant surfaces being visible from positions external to the outer peripheral surface on each opposing side of the main body along the second transverse axis; and wherein the implant needle further comprises a slot that extends in the longitudinal direction of the needle main body, the slot being defined by a pair of parallel edges, the pair of edges being parallel with each other and the main body axis and wherein the edge point and the two cutting outer edges of the second slant surfaces are configured to produce an incision shorter than an outer diameter of the implant needle and wherein the slot is configured such that less than an entire cross sectional area of a cylindrical tube with a diameter equivalent to the outer diameter of the implant needle has to be displaced during implant insertion.

2. The implant needle according to claim 1, wherein the first slant surface is provided as a pair of first slant surfaces symmetric with respect to the main body axis.

3. The implant needle according to claim 2, wherein each second slant surface is contiguous to a respective one of the first slant surfaces.

4. The implant needle according to claim 1, wherein the receiving portion is contiguous to the taper-shaped tip portion.

5. The implant needle according to claim 1, wherein the parallel edges defining the slot are non-cutting edges.

6. The implant needle according to claim 1, wherein the slot is symmetric with respect to the main body axis.

7. The implant needle according to claim 1, wherein the hollow needle main body has a round cross-section or an oval cross-section.

8. The implant needle according to claim 1, wherein one or more of the non-cutting edges are rounded.

9. The implant needle according to claim 1, wherein the hollow needle main body has a U- or V-shaped cross section in at least one of the receiving portion and the taper-shaped tip portion.

10. The implant needle according to claim 1, wherein the hollow needle main body has a diameter of 0.6 mm to 1.2 mm.

11. The implant needle according to claim 1, wherein the inner and outer edges of the first slant surface are rounded.

12. The implant needle according to claim 11, wherein the inner edge of the second slant surface and the inner and outer edges of the first slant surface have an abrasive material blasted finish.

13. The implant needle according to claim 1, wherein the non-cutting edge of the second slant surface has an abrasive material blasted finish.

14. A method for manufacturing an implant needle, comprising:

providing a hollow needle main body having a lumen surrounded by a peripheral wall;

producing a receiving portion configured to receive an implant and provided in the hollow needle main body; and producing a taper-shaped tip portion by cutting a tip portion of the hollow needle main body, wherein, when viewed from a position diametrically opposite the edge point, the taper-shaped tip portion tapers inwardly toward an edge point;

wherein the taper-shaped tip portion is produced with a first slant surface contiguous to an outer peripheral surface of the hollow needle main body and formed at a predetermined angle with respect to an axis of the needle main body, and a pair of second slant surfaces each symmetric with respect to the edge point and the axis of the needle main body and formed at a larger angle with respect to the axis of the needle main body than the predetermined angle, wherein an outer edge of each second slant surface is produced as a cutting edge which meet at and are contiguous to the edge point and thereby define a non-rounded pointed tip at the edge point, wherein inner and outer edges of the first slant surface are provided as non-cutting edges and an inner edge of each second slant surface is provided as a non-cutting rounded edge;

wherein the needle main body defines a first transverse axis extending perpendicular to the main body axis and intersecting both the main body axis and the edge point, and a second transverse axis extending perpendicular to both the main body axis and the first transverse axis and intersecting the main body axis, the first slant surface being visible from a position external to the outer peripheral surface on the first transverse axis diametrically opposite the edge point, a respective one of the pair of second slant surfaces being visible from positions external to the outer peripheral surface on each opposing side of the main body along the second transverse axis;

wherein the step of forming the taper-shaped tip portion includes configuring the edge point and the two cutting outer edges of the second slant surfaces to produce an incision shorter than an outer diameter of the implant needle; and wherein the method further includes forming a slot that extends in the longitudinal direction of the needle main body, the slot being defined by a pair of parallel edges, the pair of edges being parallel with each other and the main body axis the slot being configured such that less than an entire cross sectional area of a cylindrical tube with a diameter equivalent to the outer diameter of the implant needle has to be displaced during implant insertion.

15. Method according to claim 14, further comprising producing the non-cutting edges of the first slant surface by applying abrasive material blasting.

\* \* \* \* \*